United States Patent [19]

Linkow

[11] Patent Number: 5,547,378
[45] Date of Patent: Aug. 20, 1996

[54] APPARATUS AND METHOD FOR CLOSING A SINUS OPENING DURING A DENTAL IMPLANT OPERATION

[76] Inventor: Leonard I. Linkow, 1530 Palisade Ave., Fort Lee, N.J. 07024

[21] Appl. No.: 327,458

[22] Filed: Oct. 21, 1994

[51] Int. Cl.$^6$ ..................................................... A61C 8/00
[52] U.S. Cl. .......................... 433/173; 433/176; 433/215; 623/10
[58] Field of Search ..................................... 433/173, 174, 433/175, 176, 215; 623/10; 446/220, 222

[56] References Cited

U.S. PATENT DOCUMENTS

| | | | |
|---|---|---|---|
| 3,088,242 | 5/1963 | Rockovits | 446/220 |
| 3,108,396 | 10/1963 | Dorman | 446/220 |
| 4,430,760 | 2/1984 | Smestad | 623/10 |
| 4,599,085 | 7/1986 | Reiss et al. | 433/173 X |
| 4,657,548 | 4/1987 | Nichols | 623/10 |
| 4,682,951 | 7/1987 | Linkow | 433/173 |

*Primary Examiner*—Robert P. Swiatek
*Assistant Examiner*—Yvonne R. Abbott
*Attorney, Agent, or Firm*—Darby & Darby, P.C.

[57] ABSTRACT

An apparatus and method by which a sinus lift operation can be continued even when there is a tear in the Schneiderian membrane covering the floor of the sinus cavity. A channel is created through the maxillary bone of a patient in an edentulous region where a dental implant is to be installed. A balloon is then inserted into the channel such that its closed end extends into the sinus cavity then its open end or lips are adjacent the open end of the channel at the surface of the dental crest. The lips are then fasten to the dental crest, for example, by adhesive. Bone chips and bone fragments are inserted into the balloon such that a lower portion of the sinus cavity is filled with the balloon portion that contains bone chips. Bone chips continue to be inserted into the balloon until the channel leading to the dental crest is completely filled with the bone chips. At this point, the crest is closed and time is allowed to pass so that the bone fragment can fuse with each other and with the surrounding bone. This creates additional bone in the edentulous region which will accommodate dental implants.

14 Claims, 4 Drawing Sheets

APPARATUS AND METHOD FOR CLOSING A SINUS OPENING DURING A DENTAL IMPLANT OPERATION

BACKGROUND OF THE INVENTION

This invention relates to apparatus and a method of augmenting the maxilla of a candidate for a dental implant by filling part of the patient's maxillary sinus cavity with bone and, more particularly, to a device that closes the sinus cavity when the Schneiderian membrane is torn during surgery intended to lift the membrane from the floor of the sinus cavity and add bone under the membrane. The maxillary sinuses of a person are located on each side of the maxilla between the canine eminence and the tuberosity. The lowest point of the sinus floor usually lies superior to the first molar and the second premolar. However, maxillary sinus shapes vary greatly from one side of a person's face to the other, and from individual to individual.

As a person ages, the maxillary sinuses grow at the expense of the bone. Also, disease may cause resorption of the bone surrounding the sinus. When bone loss occurs between the sinus floor and the dental arch, the feasibility of using maxillary dental implants is decreased.

Dental or oral implants are blades or screws with attached posts. These implants are surgically implanted in a patient's mandible or maxilla along the occlusal plane. The implantation is achieved by exposing the bone with an incision through the gum tissue and creating a groove or bore in the bone with a burr or drill. The implant blade is then wedged into the groove or bore so that the post protrudes. Then the tissue is sutured about the bone and the base of the post. Finally, the post is used to mount an artificial dental appliance, such as a bridge. This procedure can be carried out in stages over several months.

A patient with an enlarged maxillary sinus has little bone in the maxillary dental arch for accommodating the insertion of an implant. Consequently, the implantation procedure may result in the penetration of the Schneiderian membrane on the sinus floor and the sinus itself. This may promote sinus infection and may result in the implant being only loosely held in the remaining bone, so that it fails to function effectively as a support for artificial teeth.

In U.S. Pat. No. 4,521,192 of the present inventor, there is suggested a technique for lifting the Schneiderian membrane and locating bone fragments beneath it in order to thicken the bone at the sinus floor by regrowth of new bone around the inserted the bone fragments. According to this suggestion, an implant is used which has a basket or cradle built into the blade portion. This basket is open toward the groove in the patient's bone and is filled with bone chips or fragments. Consequently, when the blade is wedged in the groove, the basket is moved to the base of the groove which, if the Schneiderian membrane is exposed, pushes the membrane upward into the maxillary sinus cavity.

The depth at which the blade of an implant is located in the patient's bone cannot be varied to any great extent with this prior apparatus. Thus, with this prior device, in which the basket is fixed to the blade portion of the implant, there is little control over the degree to which the Schneiderian membrane is lifted. This limits the oral surgeon's ability to increase the thickness of bone at the floor of the sinus cavity and to make it suitable for the retention of the implant.

Another technique for augmenting the mandible of a patient with additional bone in order to support a dental implant is disclosed in U.S. Pat. No. 4,682,951 of the present inventor. According to the disclosure in that patent a bone chip container which is adjustably secured to the implant is used for installing the implant in the maxilla of a patient in which the bone of the dental arch in an edentulous span is thin because of a descending maxillary sinus. In using the device, an edentulous area of the dental arch of the maxilla is exposed. A groove is made in the bone mesial and distal to the floor of the sinus, and up to the Schneiderian membrane, which membrane lies on the floor of the maxillary sinus. In addition a larger opening is made through the bone toward the center of the groove. Then an especially designed sinus lift implant is installed in the groove.

The sinus lift implant has a container which is open at one side such that it is in the form of a cradle or basket. The basket has a size such that it can pass through the opening at the center of the groove made in the bone. Threaded apertures are located in the bottom of the basket of the blade and threaded shafts engage these apertures. The blade or base portion of the implant is narrow, at least at its ends, so that it can be wedged tightly in a portion of the groove in the bone at such a depth such that the base does not extend downwardly from the maxilla beyond the existing bone of the dental arch. One or more posts project downwardly from the base and can be used to mount an artificial tooth structure from the maxilla.

During installation, the open basket is filled with bone chips, either natural or artificial. Then the basket is passed up into the large opening in the maxilla below the Schneiderian membrane. The blade portions (mesial and distal) to the basket are then tapped into place so that the implant is wedged in the groove and the basket is at least flush with the alveolar crest. Access to the ends of the threaded shafts are provided through the bottom of the apertures in the base so that the shafts can be rotated. Rotation of these shafts raises, lowers or tilts the basket to redefine the shape and thickness of the sinus floor. The basket is then moved high into the maxillary sinus, although still below the Schneiderian membrane. Its base is now well above the alveolar crest so that it is easy to suture close the tissues beneath it.

Once in position, the gum tissue is sutured closed over the base portion. During a period of several weeks or months, new bone will grow and fuse with the surrounding bone and chips. This results in a thicker bone area enclosing the implant and a reduction in the size of the sinus. After the formation of the new bone, the artificial tooth structure is mounted on the post of the implant, which post protrudes beyond the gum tissue.

The posts themselves can be made independently from the implant itself, thus allowing the implant to be completely submerged during the healing process.

SUMMARY OF THE INVENTION

The present invention is directed to eliminating the need to halt a sinus lift operation when the Schneiderian membrane is torn, by inserting a balloon into the opening in the torn membrane and essentially using it to create a cavity into which bone fragments are inserted for the purpose of augmenting the maxilla so it can better support a dental implant.

In an illustrative embodiment of the invention a tiny balloon, e.g. a finger type balloon, is pushed into the sinus opening while the lips of the balloon are glued to the bony walls of the crestal bone which surround the central opening. When the glue dries a small air pump may be inserted inside of the balloon and is used to pump it up so it can closely adapt to the inner walls of the sinus.

At the same time, bone from the iliac crest, freeze dried bone, bone from the symphysis, synthetic bone such as calcite (non-resorbable) and osteogen (resorbable) hydroxyapatite, as well as any other acceptable bone elements are syringed into the balloon as the air pressure is eliminated. Enough of the bone elements are syringed into the balloon as is necessary to achieve the desired morphological shape of the sinus walls. However, the bone does not fill up the entire sinus at any time.

The reason for inserting the air in the balloon is only to give shape to the balloon and make it easier to introduce of the bone elements. Thus, helium or some other gas may be used to inflate the balloon and in some instances inflation may not be necessary at all.

BRIEF DESCRIPTION OF THE DRAWINGS

The foregoing and other features of the present invention will be more readily apparent from the following detailed description and drawings of an illustrative embodiment of the invention in which.

DESCRIPTION OF AN ILLUSTRATIVE EXEMPLARY EMBODIMENT

Figure 1:
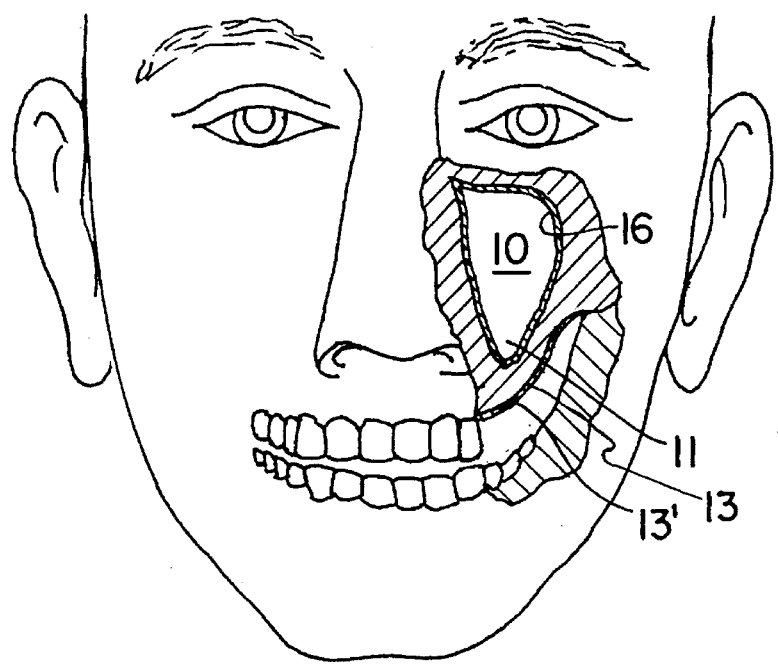
FIG. 1 is a schematic view of the face of a patient with a low maxillary sinus showing a portion transparent so that mandible and maxillary bones, the teeth and the maxillary sinus cavity are visible.

FIG. 1 illustrates an enlarged descending maxillary sinus cavity 10 of a potential dental implant patient. The descending portion 11 could be the result of disease or it could be congenital. Regardless of the cause, the effect is to produce a very small amount of bone between the sinus cavity 10 and the alveolar ridge crest 13. Thus, if a root form or blade-type of dental implant is to be installed in an edentulous region in that vicinity, there is very little bone in which the implant can be anchored.

Figure 2:
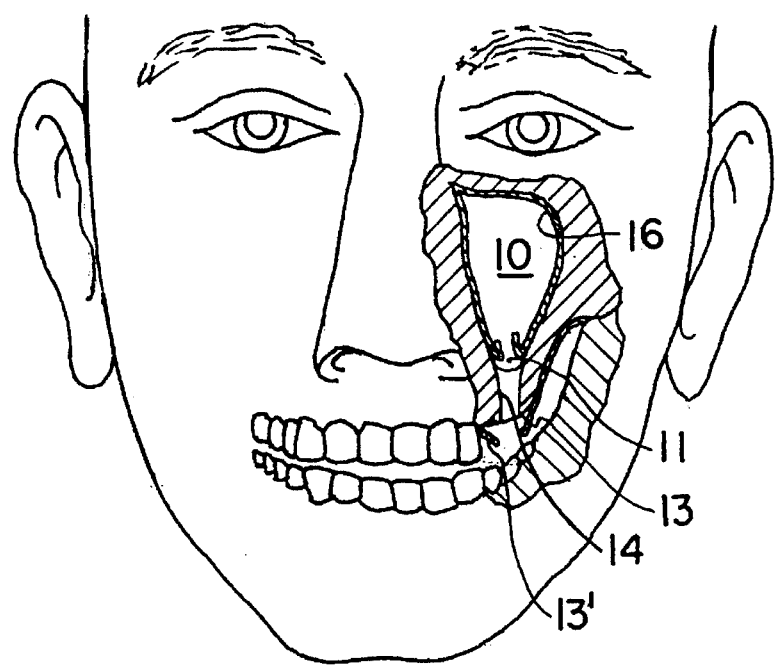
FIG. 2 is a view similar to FIG. 1, but showing the removal of maxillary bone and the tearing of the Schneiderian membrane during a sinus lift operation.

The interior of the sinus cavity 10 is covered with a membrane known as the Schneiderian membrane 16. During a sinus lift operation an incision is made in the tissue 13' covering the alveolar ridge crest 13. The tissue is then reflected to expose the underlying maxillary bone. Then using a dental drill a channel 14 is created in the bone from the surface of the ridge crest 13 to the cavity 10 as shown in FIG. 2. During this process, care must be taken to avoid tearing the Schneiderian membrane 16 which covers the floor of the sinus cavity 10. The Schneiderian membrane is, however, separated from the floor of the sinus cavity and is lifted upward into the cavity. Various means are then used to pack bone chips into the lower area 11 underneath the Schneiderian membrane, which membrane acts to prevent bacteria from traveling from the site of the implant into the sinus cavity.

Figure 3:
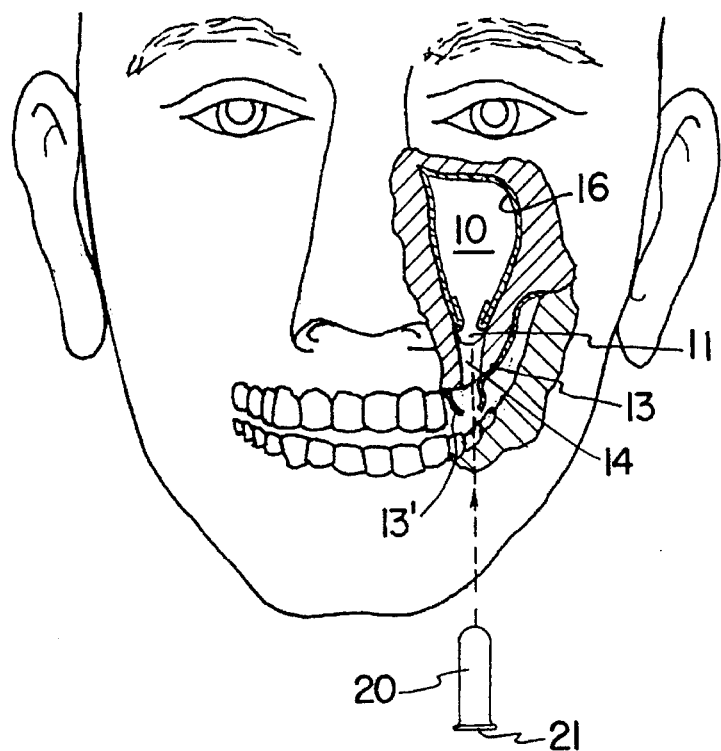
FIG. 3 is the same as FIG. 2, but illustrating a balloon useful in practicing the present invention.
Figure 4:
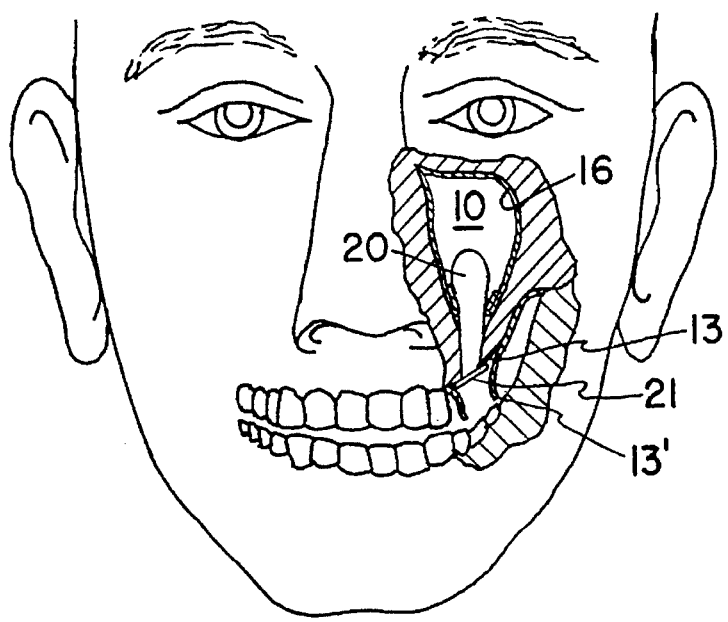
FIG. 4 shows the balloon of FIG. 3 inserted through a tear in the Schneiderian membrane and into the maxillary sinus cavity.

As shown in FIG. 2 during the course of the sinus lift operation when the channel 14 is drilled from the ridge crest 13 into the cavity 10, the Schneiderian membrane 16 may be torn. If an attempt were made to lift the sinus floor by inserting bone chips into channel 14, problems would arise. First, there would be nothing to prevent the bone fragments from entering into the cavity 10 and rattling around freely in the cavity. Second, bacteria and other germs could enter the cavity through the channel 14 and the torn Schneiderian membrane 16. The present invention proposes to address this problem by means of a small rubber balloon 20 shown in FIG. 3. As shown in FIG. 4 the balloon 20 is inserted in the channel 14 so that it extends into the sinus cavity 10. The lips 21 of the balloon are glued or otherwise fastened to the exposed bone of the alveolar ridge crest in the area surrounding the channel 14. At the end of the surgery, when the tissue covering ridge 13 is returned to its normal position and stitched in place, it will cover over the lips 21 of the balloon 20.

Figure 5:
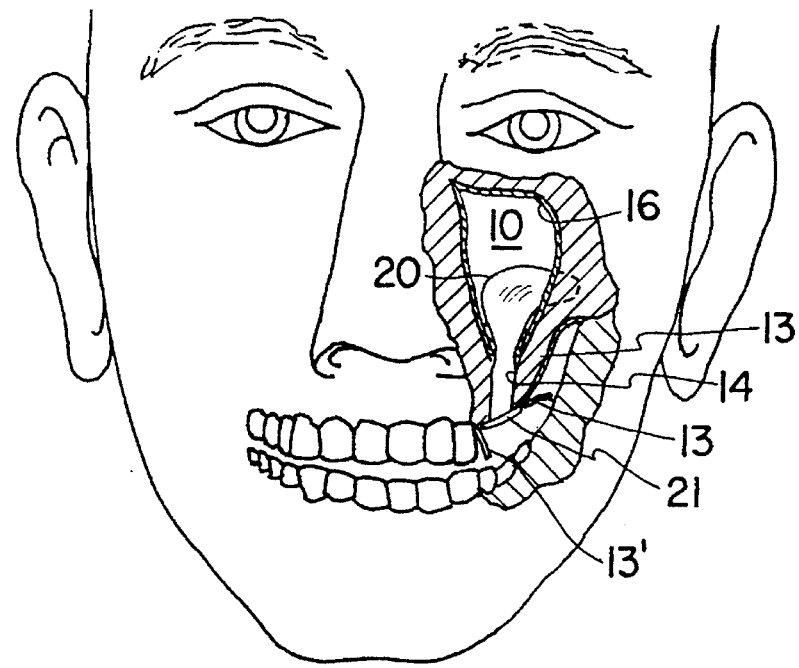
FIG. 5 illustrates the balloon in an inflated state in the sinus cavity.

Prior to closing the tissue, air, helium or some other gas is injected into the balloon through its lips. The result is to cause the balloon to at least partially inflate and conform to the inner walls of the sinus cavity as shown in FIG. 5. If the balloon is made so that it naturally stays open, the inflation step can be eliminated.

It should be noted that the dotted outline illustrating the sinus cavity 10 in FIGS. 1–7 represents only a portion of the cavity at a particular cross section. Just above the alveolar ridge crest the cavity actually extends beyond the dotted area in the mesial or distal direction, as well as in a bucco-lingual direction as shown by the balloon 20 in FIG. 5.

Figure 6:
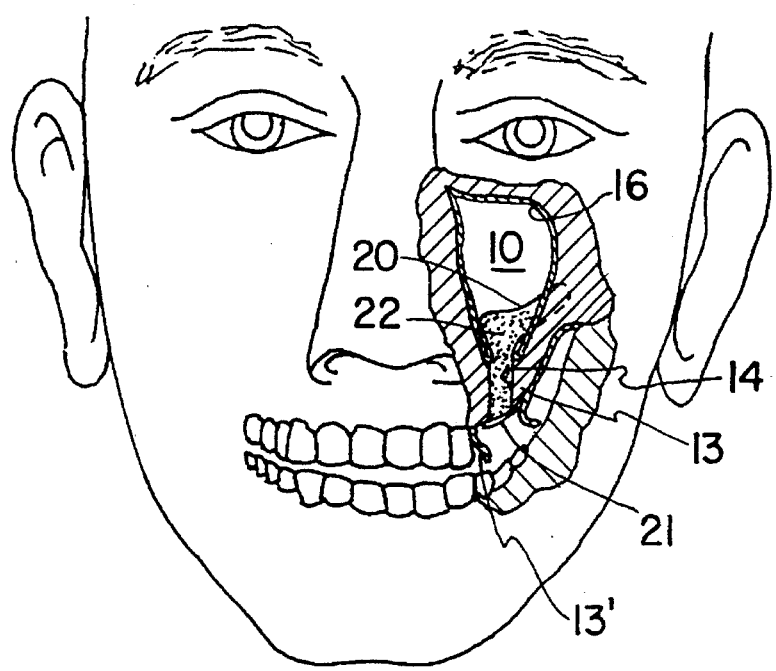
FIG. 6 is a view of the balloon with bone fragments inserted.

After the balloon is put in place and inflated, if necessary, or simultaneously with inflation thereof, bone fragments 22 are syringed into the interior of the balloon and eventually act to displace the air in the balloon (FIG. 6). This process is continued until the lower portion of the sinus cavity 11 and the channel 14 are filled with bone chips. The top portion of the balloon acts as a new raised sinus floor under which the new bone 22 is deposited. These bone fragments may be bone from the iliac crest, freeze dried bone from the symphysis, or synthetic bone such as calcite (non-resorbable) and osteogen (resorbable) hydroxyapatite.

There are catheters used for balloon angioplasty which are ideal for use in the present invention. The catheter allows the balloon at its end to be inserted in the channel. Further, it already has a source of gas, e.g. helium, for inflating the balloon if necessary.

Once the balloon is in place and filled with bone, the channel 14 at the surface of the ridge adjacent the balloon lips 21 may be closed with a cap and the tissue of the ridge crest sutured back into place. Over a period of time, if the balloon is made of resorbable material, the balloon will dissolve and new bone will grow under the raised sinus floor using the bone fragments as starting points. The end result will be an augmented maxilla suitable for implantation.

The balloon may also be formed in two parts where the upper part is non-resorbable and the lower part leading to the lips is resorbable. In such a situation, the balloon continues to act as a Schneiderian membrane even after the lower portion has dissolved, allowing new bone to grow underneath it.

Figure 7:
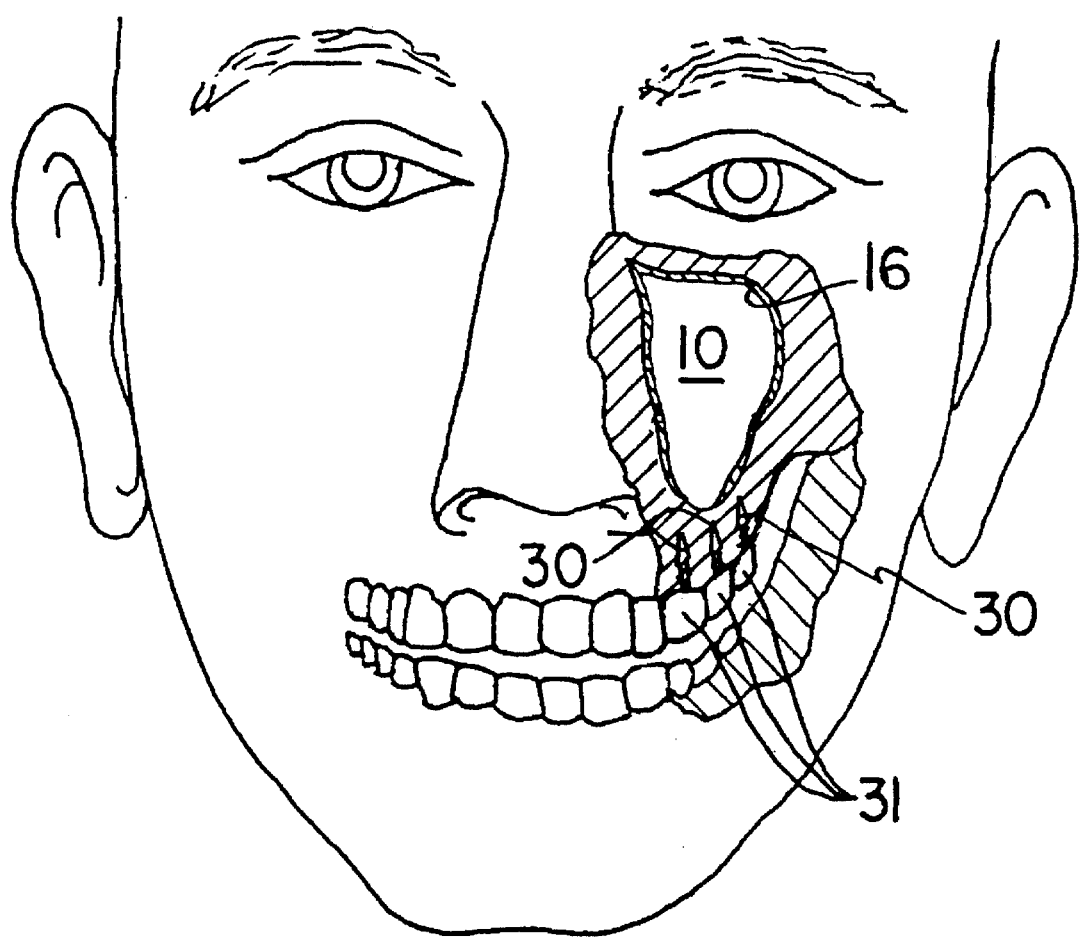
FIG. 7 illustrates four root form implants installed in bone augmenting the maxilla as a result of a sinus lift operation according to the present invention.

Whenever the new bone has been firmly established as confirmed by x-rays, the tissue covering the alveolar ridge crest 13 may again be opened and this time dental implants, for example, blades or root-form implants 30, may be inserted into the new bone in such a manner that they support artificial teeth 31 in the edentulous region. This is shown in FIG. 7.

The balloon for use in the present invention may be manufactured from various types of material. These materials can be slowly resorbable and elastic, inert and acceptable biocompatably with the bone in the area. For example, the material can be similar to Gortex except that it should be resorbable, such as polylactate.

As an alternative, the material can be elastic inert and non-resorbable as described above. In a further embodiment, the entire balloon could be non-resorbable and could remain in place to support the material bone that is within it. Whether the balloon is resorbable or non-resorbable will have an effect on the future reestablishment of a Schneiderian membrane. For example, if the balloon remains in place the Schneiderian membrane may not grow over it. Thus the preferred embodiment is to use a slowly resorbable balloon material for two reasons:

1. By slowly resorbing, it gives the bone that was syringed into the balloon a chance to mature so that when it finally resorbs, the bone will be solid and non-removable.

2. The Schneiderian membrane, while present, may stimulate or irritate the mucus membrane of the nose cavity to regenerate a new Schneiderian membrane by the time it resorbes.

Other materials which can be used for the balloon include Bovine collagen; polyethylene; resorbable Polylactic acid; resorbable lactic acid used with an elastic (resorbable or non resorbable) membrane that is sufficiently permeable to allow blood and nutrients to enter into the balloon by osmosis and contact the bone within, which promotes the growth of this bone. Also, Calcitek absorbable collagen, or Hematex by Bioplex Co. which is absorbable collagen hemostat can be used.

By means of the present invention, continuation of the sub-antral bone augmentation can be accomplished immediately after a large perforation of the Schneiderian membrane. Without the present invention, the procedure would have to be aborted once the Schneiderian membrane was penetrated.

While the invention has been particularly shown and described with reference to a preferred embodiment thereof, it will be understood by those skilled in the art that various changes in form and details may be made therein without departing from the spirit and scope of the invention.

What is claimed is:

1. A method of reducing the maxillary sinus of a patient, comprising the steps of:

forming an incision through the mucoperiosteal tissue at an edentulous site to expose underlying maxillary bone of the dental arch mesial and distal to the sinus;

creating an opening completely through the bone and the Schneiderian membrane at the floor of the sinus mesial-distal and bucco-palata;

placing a balloon through the opening so that the closed end of the balloon is within the sinus cavity;

securing the lips of the open end of the balloon to the surface of the maxillary bone of the dental arch surrounding the opening and leaving a passageway through the lips to the interior of the closed end of the balloon within the sinus;

inserting bone fragments through the balloon passageway into the interior of the closed end of the balloon previously placed within the sinus cavity;

closing the opening through the bone; and closing the tissue over the bone.

2. The method of claim 1 further including the step of at least partially inflating the closed end of the balloon placed in the sinus after the lips of the balloon are secured to the surface of the maxillary bone.

3. The method of claim 2 wherein the balloon is inflated with air.

4. The method of claim 2 wherein the balloon is inflated with helium.

5. The method as in claim 1 further including the steps of reopening the tissue after a sufficient period of time has elapsed for the bone fragments inserted into the closed end of the balloon placed in the sinus cavity to fuse and adhere to the surrounding bone of the cavity;

forming at least one opening in the dental arch in the edentulous site which extends into the inserted bone;

installing a dental implant in the at least one opening; and closing the tissue around a projecting portion of the dental implant.

6. The method of claim 5 wherein at least the closed end portion of the balloon within the sinus cavity is of resorbable material and the step of reopening is delayed until the closed end portion of the balloon has resorbed.

7. The method of claim 1 wherein the balloon is of resorbable material.

8. Apparatus as claimed in claim 1 wherein the closed end of the balloon is of resorbable material and the portion towards the open end of the balloon is of non-resorbable material.

9. Apparatus for closing a hole in the Schneiderian membrane of a maxillary sinus cavity formed during a dental implant operation comprising:

a balloon of elastic material with a closed end and an open end having a passage opening surrounded by lips, said balloon being collapsible and of a size small enough for said balloon closed end to pass through a channel in a patient's dental maxillary arch extending to the sinus cavity in an edentulous region such that its closed end extends into the sinus cavity and the lips at its open end extend out of the channel, said balloon closed end being at least partially inflatable and of sufficient strength to withstand the injection of bone fragments through said balloon open end into said closed end while in the sinus cavity; said balloon having a maximum size such that it may be substantially uncollapsed in the sinus cavity; and fastening means on the outside of the lips at the open end of the balloon such that the outside of the lips of the balloon may be fastened to the opening at the dental arch.

10. Apparatus as claimed in claim 9 wherein the balloon is of resorbable material.

11. Apparatus as claimed in claim 9 wherein the closed end of the balloon is of resorbable material and the portion towards the open end of the balloon is of non-resorbable material.

12. Apparatus as claimed in claim 9 wherein the entire balloon is of non-resorbable material.

13. Apparatus as claimed in claim 9 wherein at least said balloon closed end is of a permeable material to permit passage of blood and nutrients into its interior by osmosis when the balloon closed end is in the sinus cavity.

14. Apparatus as claimed in claim 9 wherein the material of the said at least balloon closed end is selected from the group comprising polylactate, bovine collagen, polyethylene, resorbable Polylactic acid, resorbable lactic acid with an elastic membrane, absorbable collagen, and absorbable collagen hemostat.

* * * * *